United States Patent
Auerswald et al.

(10) Patent No.: US 9,128,035 B2
(45) Date of Patent: Sep. 8, 2015

(54) SENSOR FOR REGISTERING AN ANALYTE CONCENTRATION

(71) Applicant: Endress + Hauser Conducta Gesellschaft für Mess- und Regeltechnik mbH + Co. KG, Gerlingen (DE)

(72) Inventors: Lothar Auerswald, Dobeln (DE); Jorg Uhle, Limbach-Oberfrohna (DE); Tobias Mieth, Dresden (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 0 days.

(21) Appl. No.: 14/095,330

(22) Filed: Dec. 3, 2013

(65) Prior Publication Data
US 2014/0151223 A1 Jun. 5, 2014

(30) Foreign Application Priority Data

Dec. 5, 2012 (DE) .......................... 10 2012 111 813

(51) Int. Cl.
*G01N 27/28* (2006.01)
*G01N 27/414* (2006.01)

(52) U.S. Cl.
CPC .............. *G01N 27/28* (2013.01); *G01N 27/286* (2013.01); *G01N 27/414* (2013.01)

(58) Field of Classification Search
CPC ............ G01N 27/333; G01N 27/3335; G01N 27/4035; G01N 27/414
USPC .................................................. 204/416–420
See application file for complete search history.

(56) References Cited

U.S. PATENT DOCUMENTS

| 5,833,824 | A | 11/1998 | Benton |
| 6,117,292 | A | 9/2000 | Ahmad |
| 6,153,070 | A | 11/2000 | Mauerer |
| 2002/0027074 | A1 | 3/2002 | Tominaga |
| 2012/0247955 | A1 | 10/2012 | Yamanouchi |

OTHER PUBLICATIONS

German Search Report, German Patent Office, Munich, Jul. 15, 2013.

*Primary Examiner* — J. Christopher Ball
(74) *Attorney, Agent, or Firm* — Bacon & Thomas, PLLC

(57) ABSTRACT

A sensor for registering analyte concentration includes: a housing; arranged within the housing, a sensor element, which has a front surface pressed toward a housing wall of the housing, and the sensor element has at least one contact element for electrical contacting accommodated within the housing, an inner electrolyte, which is in contact with a medium surrounding the housing via an electrochemical, liquid junction arranged in a housing wall, and a reference electrode extending into the inner electrolyte, wherein there is arranged within the housing a flexible circuit card, which includes at least a first conductive trace, which is connected with the at least one contact element of the sensor element, and at least a second conductive trace, which serves as potential sensing element of the reference electrode.

21 Claims, 3 Drawing Sheets

SENSOR FOR REGISTERING AN ANALYTE CONCENTRATION

TECHNICAL FIELD

The invention relates to a sensor for registering an analyte concentration in a measured medium.

BACKGROUND DISCUSSION

Determining concentration of an analyte in a measured medium plays an important role in many industrial applications, for example, in chemical or pharmaceutical technologies, in foods technology, in biotechnology, as well as also in non-industrial, analytical applications, for example, in environmental measurements technology. Applied for determining ion concentrations frequently in the laboratory, as well as also in industrial process plants, are sensors, which have a sensor element bearing an analyte sensitive component. The analyte sensitive component can be, for example, an analyte sensitive membrane. Thus, for example, the glass membrane of the known pH glass electrode is sensitive to the concentration of H+, respectively $H_3O+$, ions in a measured medium.

Alternatively, the analyte sensitive component can also be a semiconductor element, for instance, a component comprising an EIS structure, such as, for example, an ion sensitive, field effect transistor (ISFET) or a capacitor with an EIS structure, whose capacitance depends on the concentration of the substance to be determined. The acronym "EIS" stands for "Electrolyte Insulator Semiconductor", i.e. the sensor has a layer structure with, applied on a semiconductor layer or on a semiconductor substrate, at least one insulating layer, which, in measurement operation of the sensor, is in contact with an electrolyte, namely the measured medium. Arising at the interface between the insulating layer and the measured medium is a voltage drop. Through suitable choice of the insulating layer, especially by providing an analyte sensitive coating on, or as a component of, the insulating layer, the sensitivity of the sensor can be set in such a manner that the voltage drop can serve as a measure for the analyte concentration. Thus, for example, the voltage drop at the interface between a tantalum(V) oxide ($Ta_2O_5$) layer and an aqueous measured solution depends essentially on the pH value of the measured solution. Through application of other layer structures, EIS sensor elements can be formed, which are sensitive in corresponding manner for other ions. By immobilizing suitable detector structures, which can comprise e.g. enzymes, on the EIS structure, it is also possible by means of such a sensor to measure concentrations of non-ionic substances, e.g. glucose or penicillin.

The already mentioned ion-sensitive field effect transistor has likewise such an EIS structure. The transistor gate of the ISFET is in the case of a pH-sensitive ISFET, for example, formed by a pH sensitive, insulating layer, which can comprise $Ta_2O_5$. The charge carrier density in the semiconductor channel between source and drain of the ISFET then depends correspondingly on the pH value of the medium in contact with the gate. German Patent DE 198 57 953 A1, for example, describes a sensor for measuring ion concentrations, respectively the pH value, of a liquid using an ISFET.

Such sensor elements with an analyte sensitive component, especially semiconductor based elements, are frequently embodied in the form of a platelet or chip, for example, as a chip or chip array, with front- or rear, contact elements for electrical contacting of the analyte sensitive component. Sensors with such sensor elements are frequently embodied as rod-shaped measuring probes, which comprise a medium immersible housing, in which the sensor element is so arranged that its analyte sensitive component contacts the measured medium. In such case, the contact elements for electrical contacting of the analyte sensitive component, via which the sensor element is connected with a sensor electronics, and the sensor electronics itself, are arranged protected within the housing. The measuring probe can be connectable via a cable or wirelessly with a superordinated unit, for example, a measurement transmitter or a bus coupler. The superordinated unit can supply the measuring probe with energy, respectively receive, and further-process, measuring signals output from the sensor electronics, or it can output signals to the sensor electronics. Examples of such sensors are disclosed in U.S. Pat. No. 6,117,292, U.S. Pat. No. 6,153, 070 or European EP 1 396 718 A1.

Described in European EP 1 396 718 A1 is a sensor having an ISFET as sensor element. By means of a pressure exerting part, the ISFET is pressed at a rear surface facing away from its ion sensitive surface region against an end face of a sensor housing. The pressure exerting part has a central opening, which exposes the ion sensitive surface region of the ISFET, while the source connection and the drain connection of the ISFET are arranged in an interior of the sensor protected from contact by the measured medium. The pressure exerting part is connected with the sensor housing by means of a surrounding ultrasonic weld excluding the medium.

An internal tube extending within the housing divides the housing interior of the sensor housing into a sensor inner space and a sensor intermediate space. The sensor intermediate space serves as reference electrode space, i.e. it contains a reference electrolyte, into which a reference electrode extends. Led through the sensor inner space are connection wires connected with front- or rear contact elements of the ISFET for contacting source and drain of the ISFET. The connection wires serve for connection of the ISFET with a display device of the sensor. The sensor inner space is back-filled from the internal tube to the rear surface of the ISFET with a potting compound, for example, one based on an epoxy adhesive, in order to provide mechanical support for the ISFET.

European EP 1 396 718 A1 shows, by way of example, the previously always followed principle of having a sensor inner space, which serves for the contacting and the guiding of the potential sensing wires of the sensor element, and an electrolyte filled, intermediate space, in which the reference electrode, embodied, as a rule, as a reference electrode of second type, is arranged. Manufacturing these sensors of the state of the art embodied according to this principle requires a number of individual working steps and is, consequently, quite complex and expensive.

Moreover, the sensor housing of such sensors frequently contains, connected with the potential sensing wires, a sensor circuit, frequently an electronic sensor circuit, also referred to as the sensor electronics, which serves for initial processing, especially amplification and, in given cases, digitizing, of the measurement signal. Penetration of moisture into the sensor electronics can lead to failure of the sensor. Consequently, great effort must be applied, in order to assure the sealing of the electrolyte filled, reference electrode space relative to the sensor electronics, which is, as a rule, likewise accommodated in the sensor housing.

SUMMARY OF THE INVENTION

It is, therefore, an object of the present invention to provide an electrochemical sensor of the initially described type, which is improved for overcoming the mentioned disadvantages. Especially, the sensor should be manufacturable with lesser effort and assure an improved sealing of the region of the sensor housing containing the sensor circuit relative to the inner electrolyte accommodated within the housing.

The object is achieved according to the invention by a sensor for registering an analyte concentration which includes:

a housing;

arranged within the housing, a sensor element, which has a front surface pressed toward a housing wall of the housing, wherein the housing wall has an opening exposing an analyte sensitive region of the front surface, and wherein the sensor element has at least one contact element for electrical contacting;

accommodated within the housing, an inner electrolyte, which is in contact with a medium surrounding the housing via an electrochemical, liquid junction arranged in a housing wall; and a reference electrode extending into the inner electrolyte, wherein there is arranged within the housing a flexible circuit card, which includes at least a first conductive trace, which is connected with the at least one contact element of the sensor element, and at least a second conductive trace, which serves as potential sensing element of the reference electrode.

The accommodating of both the lead to the at least one contact element of the sensor element as well as also the lead to the reference electrode in a flexible circuit card permits omission of the previous dividing in two between a sensor inner space, through which connection wires of the sensor element are led, and a sensor intermediate space containing an inner electrolyte, for example, a reference electrode space containing the reference electrode immersed in a reference electrolyte. The flexible circuit card can be located directly in the conductive reference electrolyte, so that a medium-sealing of a space, in which the connection wires are led, from a space containing the inner electrolyte is no longer required. This simplifies the manufacturing of the sensor, since the complex internal tube mounting for forming an inner space separated from the inner electrolyte is no longer required. Added to this is the fact that the omission of the internal tube in the housing interior makes more space available. In this way, it is possible also to accommodate in the housing a flexible circuit card, whose length significantly exceeds the axial length of the housing. This facilitates the manufacturing of various sensor types with different housing lengths such that for connecting the contact elements of the sensor element with the sensor circuit it is not necessary to keep circuit card variants of different lengths in inventory.

If a number of contact elements of the sensor element are present, all required connection lines can be implemented as conductive traces of the flexible circuit card.

The base material of the flexible circuit card is a plastic foil, for example, a polyimide film. The conductive traces serving as connection lines for the sensor element and/or the conductive trace serving as potential sensing element in the form of a lead to the reference electrode can extend within the electrically insulating, base material or be covered by an additional coating of a plastic material, so that they/it do(es) not come in contact with the inner electrolyte.

The inner electrolyte can be contained in a first chamber formed within the housing, wherein the housing has, sealed from the first chamber, a second chamber, in which a sensor circuit, especially an electronic, sensor circuit, is accommodated, and wherein the first chamber is sealed from the second chamber, especially by means of at least one seal, through which the flexible circuit card is led. The seal can be formed especially of an elastic material. The first chamber can be formed at a front end, i.e. sensor element end, region of the housing. The second chamber can be formed in a rear, i.e. connection end, region of the housing.

The seal can comprise, for example, two or more sealing elements, which are pressed together by the inner wall of the sensor housing. The flexible circuit card can be led between the sealing elements from the first chamber into the second chamber.

The first and second conductive traces can be connected electrically conductively with the sensor circuit, wherein the sensor circuit is embodied to register via the conductive traces one or more electrical, measured variables and to process one or more, in given cases, digital, measurement signals and to output such to a superordinated unit connected with the sensor.

The sensor circuit can be arranged within the second chamber on a circuit card, which is coupled with the flexible circuit card in such a manner that the first and second conductive traces are connected electrically conductively with the sensor circuit. The circuit card comprising the sensor circuit can be embodied, for example, as a rigid circuit card. The connectors of the flexible circuit card and the circuit card carrying the sensor circuit can be matched to one another, so as to lessen the manufacturing effort further.

The material for the rigid circuit card can be an established circuit card material, e.g. a phenol- or epoxide resin based material, such as FR2, FR3, FR4, FR5, or polyimide.

In another advantageous embodiment, the sensor circuit is arranged on a section of the flexible circuit card arranged within the second chamber.

The housing of an embodiment can comprise a sensor body and an electronics housing part fixedly connected with the sensor body, wherein the sensor body has an at least sectionally tubular, sensor shaft and, frontally adjoining the sensor shaft, an end section, which includes the housing wall, toward which the front surface of the sensor element is pressed, and wherein a rear end of the sensor shaft is closed by the electronics housing part.

The electronics housing part can, especially in the form of a kind of cap, be plugged onto the sensor shaft and fixedly connected with the shaft, for example, through use of an adhesive. The sensor body can be formed of glass or a synthetic material such as a plastic, for example, PEEK, which is suitable for immersion in the measured medium. The electronics housing part is not intended for immersion in the measured medium and can, consequently, be formed of any synthetic material, such as a variety of plastic.

The already mentioned seal can be arranged in a rear end region of the sensor shaft for sealing the first, electrolyte filled chamber of the housing relative to the second chamber containing the sensor circuit. The seal can comprise at least two, especially elastic, sealing elements of synthetic material, which bear against the inner wall of the tubular sensor shaft, and which have two sealing surfaces biased toward one another, between which the flexible circuit card is clamped, so that the circuit card is led liquid tightly from the first chamber into the second chamber. The clamp seal of such type is especially easy to handle in the manufacturing of the sensor and permits an essentially safer sealing of the frontal, electrolyte filled, first chamber from the rear, second chamber, in which the sensor circuit is accommodated, in comparison to conventional sensors, in the case of which the initially described internal tube and the potential sensing lead to the reference electrode must be led through a sealing plug arranged in the sensor shaft.

The electronics housing part can include an interface for connecting to a superordinated unit. The interface can comprise, in such case, besides a mechanical interface, e.g. a plug head, which can be connected releasably with a complementary socket of a cable connected with the superordinated unit, an electrical, respectively electronic interface, via which the sensor circuit is connected for exchange of energy and data with the superordinated unit, when the mechanical interface is connected with the complementary interface of the superordinated unit or with the complementary interface of the cable connected with the superordinated unit. For this, the sensor circuit includes circuit components, which serve to provide signals to the interface. The interface can have, for example, galvanic contacts or be embodied contactlessly in the form of a capacitively or inductively coupling interface.

The reference electrode can have an at least sectionally chlorided, silver wire connected electrically conductively with the second conductive trace, for example, by way of a soldered connection. The silver wire is arranged within the first chamber of the housing and extends into the inner electrolyte serving as reference electrolyte. The inner electrolyte can be a 3 molar KCl solution. This is in electrolytic contact with the medium surrounding the housing via the electrochemical, liquid junction arranged in the housing wall. The liquid junction can be, for example, a simple bore or a porous diaphragm of a synthetic material, such as a plastic. Another option is to provide the porous diaphragm in the form of a ceramic material.

The electrically conductive connection between the reference electrode and the flexible circuit card can be arranged in a frontal, i.e. sensor element end, region of the flexible circuit card, preferably in the vicinity of the sensor element. Since the reference electrode is contacted with the flexible circuit card in the frontal end region of the sensor, absent here is the requirement existing in the case of sensors known from the state of the art for an additional, potential sensing element led over almost the entire length of the sensor from the reference electrode to the sensor circuit arranged in the rear, electronics housing part. The frontal end region of the sensor housing, in which the sensor element and the joint between the reference electrode and the circuit card are arranged, can be filled with a potting compound, for example, one based on epoxide. The potting compound serves for improved isolation of the connections, especially soldered connections, between the contact elements, respectively the reference electrode and the first conductive traces, respectively the second conductive trace, of the flexible circuit card.

Instead of using a wire soldered on the flexible circuit card as reference electrode, also a layer system arranged on the circuit card can serve as reference electrode. In this embodiment, the reference electrode can comprise, arranged on the flexible circuit card, and in electrical contact with the second conductive trace, a silver layer, which is covered, at least partially, by an AgCl layer.

For improving the signal quality, the flexible circuit card can include an additional, shielding ply.

The flexible circuit card can be equipped in the region of the sensor element with a temperature sensor, which is connected with a third conductive trace of the flexible circuit card. The third conductive trace can be connected with the sensor circuit, which, in this embodiment, is also embodied to process signals provided by the temperature sensor. Same as the potential sensing lead to the reference electrode and the connection lines of the sensor element, the third conductive trace can likewise be embedded in the electrically insulating, base material of the circuit card or covered by an additional plastics coating, so that it is not in electrical contact with the inner electrolyte. The temperature sensor as well as, in given cases, other SMD components present on the flexible circuit card are preferably, same as the joint of the reference electrode with the circuit card, arranged in the vicinity of the sensor element in a frontal end region of the housing, which supplementally can contain a potting compound.

The sensor element can comprise an EIS structure. Especially, the sensor element can comprise an ion sensitive field effect-transistor, which has, besides the analyte sensitive region serving as gate on the front surface, a source connection arranged on the front surface or on a rear surface of the sensor element facing away from the front surface and serving as contact element and a drain connection arranged on the front surface or on the rear surface of the sensor element and serving as a further contact element. In this case, the flexible circuit card has two first conductive traces, of which one is connected electrically conductively with the source connection and the other with the drain connection. The flexible circuit card can be equipped with a temperature sensor, especially one embodied as an SMD component, arranged in the vicinity of the sensor element and, such as already mentioned, connected conductively with a third conductive trace of the flexible circuit card. The two first and third conductive traces are, such as already mentioned above, connected with a sensor circuit, which is arranged in a second chamber liquid tightly separated from the first chamber of the sensor housing containing the inner electrolyte, wherein the sensor circuit serves for registering and additional processing of signals provided via the contact elements of the sensor element and/or the temperature sensor.

BRIEF DESCRIPTION OF THE DRAWINGS

The invention will now be explained in greater detail based on the example of an embodiment illustrated in the drawing, the figures of which show as follows.

DETAILED DISCUSSION IN CONJUNCTION WITH THE DRAWINGS

Figure 1:
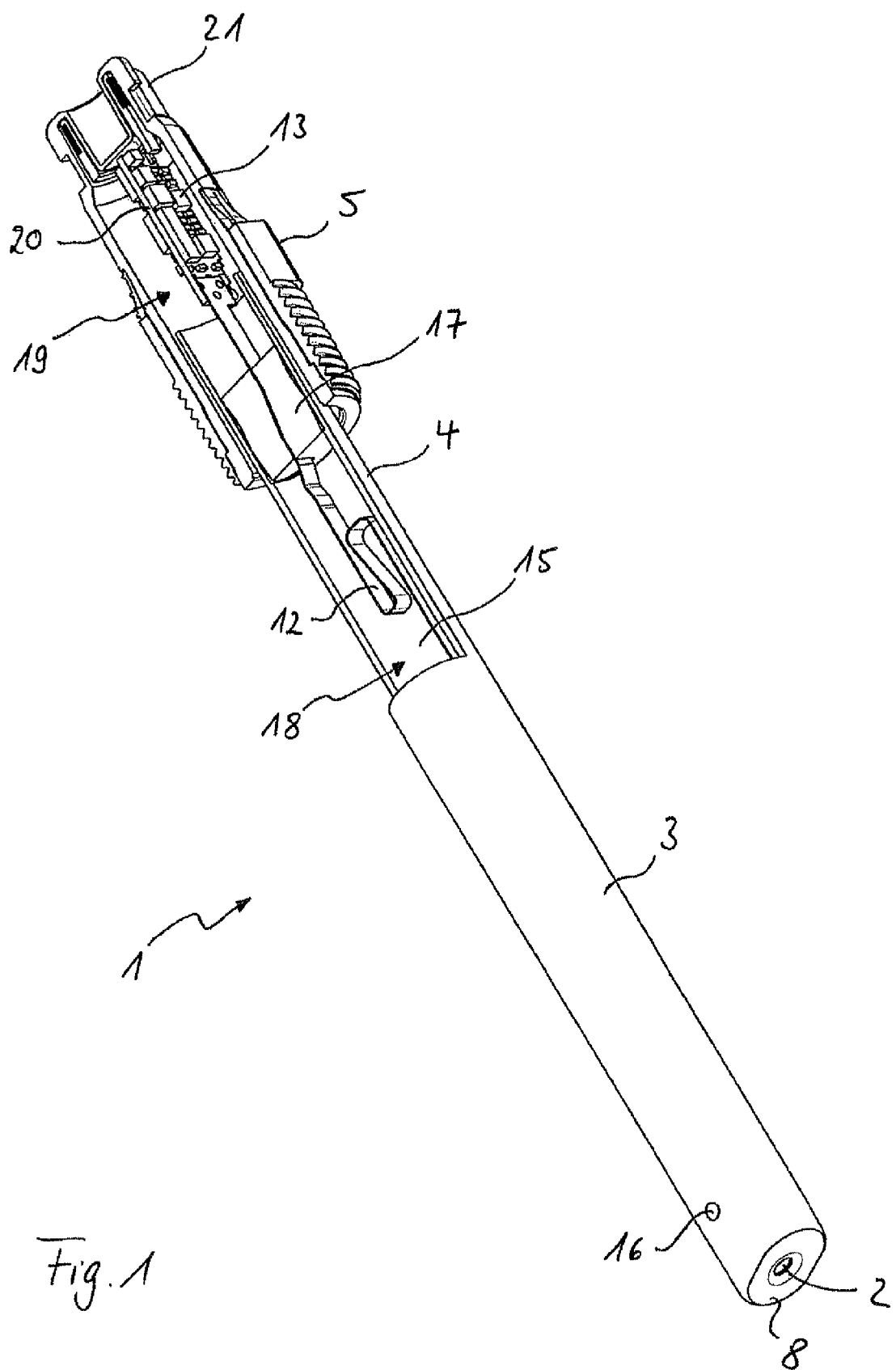
FIG. 1 is a total view of an electrochemical sensor, partially in longitudinal section.

FIG. 1 shows a schematic, longitudinal section of an electrochemical sensor 1 for measuring a pH value of a measured medium. The sensor shown here includes as analyte sensitive sensor element 2 an ion sensitive, field effect transistor. Although in the following the invention is described based on a pH sensor having a pH sensitive ISFET as sensor element, the invention is, of course, applicable for sensors having other sensor elements, especially ISFETs, respectively ChemFETs, or other sensor elements comprising EIS structures, as well as sensors having ion-, respectively analyte, sensitive membranes, which provide a signal dependent on the concentration of an analyte in a measured medium.

Sensor 1 includes a housing 3, which is formed essentially of a sensor body 4 and an electronics housing part 5 fixedly connected with the sensor body 4. Sensor body 4 can be composed of an electrically non-conductive material, for example, glass or a synthetic material, such as a plastic. In the present example, the sensor body 4 is composed of polyetheretherketone (PEEK). Sensor body 4 has a tubular sensor shaft, whose front end section (FIG. 2) is embodied to be immersed in a measured medium for measuring pH value. On the rear end, the sensor shaft of the sensor body 4 is connected fixedly with the electronics housing part 5, which is placed in the manner of a kind of cap on the rear end of the sensor shaft 4 and closes the sensor shaft 4. The electronics housing part 5 is composed of an electrically non-conductive, synthetic material, for instance, a plastic.

Figure 2:
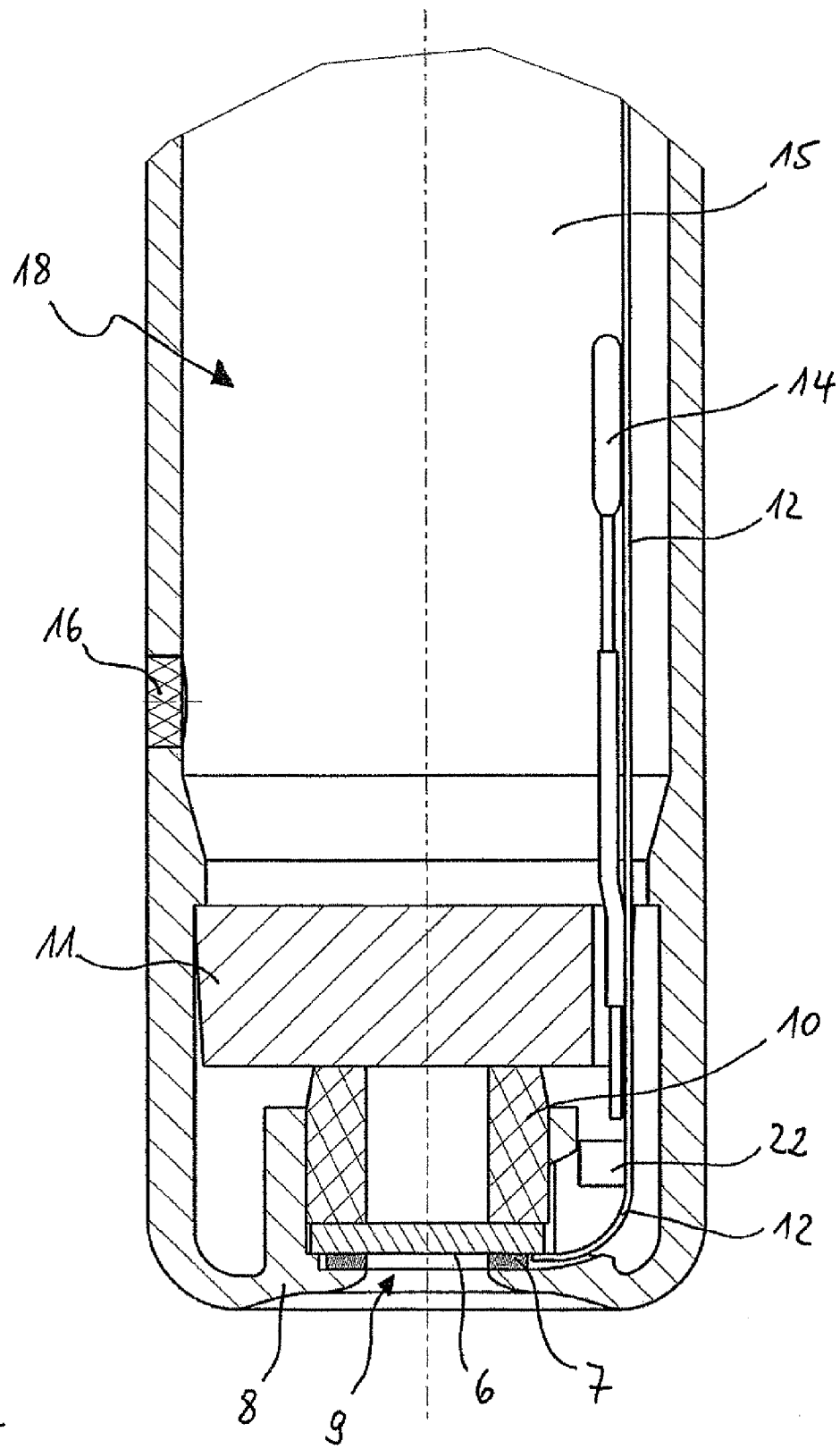
FIG. 2 is an enlarged, longitudinal section of the frontal, end section of the sensor illustrated in FIG. 1.

As is shown in detail in FIG. 2, the sensor element 2 is pressed with its front surface 6 toward a front wall 8 of the sensor body 4. Interposed between the front surface 6 and the front wall 8 is an elastic sealing element 7. Wall 8 has an opening 9, which exposes a pH sensitive surface region of the sensor element 2, so that this region, in the case of immersion of the sensor 1 into a measured medium, comes in contact with the measured medium.

Sensor element 2 is pressed against the elastic sealing element 7 by means of a pressure providing part 10 acting on its rear-side that faces away from the pH sensitive surface region. Pressure bearing part 10 can be composed, for example, of an elastomer, so that the sensor element is clamped sandwich-like between the elastic sealing element 7 and the pressure providing part 10. Pressure providing part 10 is supported on its rear by a bulwark 11 connected with the housing wall of the housing 3.

While the transistor gate forming the pH sensitive surface region of the sensor element 2 embodied as an ISFET is in contact with the medium surrounding the housing 3, source and drain of the ISFET are arranged in a region of the front surface 6 of the sensor element 2 sealed by means of the sealing element 7 from the medium in the environment of the housing 3. Contact elements serving as source- and drain connections can be arranged either, such as in the example shown here, on the front surface 6 of the sensor element 2 or on a rear surface facing away from the front surface 6.

The contact elements are connected by means of a soldered connection electrically conductively with conductive traces of a flexible circuit card 12, which extends in the axial direction through the sensor body 4. In the example shown here, the conductive traces extend within the flexible circuit card 12. They extend over the entire length of the flexible circuit card 12 and are connected with a sensor circuit 13 arranged in the connection housing part 5. In the frontal end region of the sensor body 4, a reference electrode 14 is arranged on the flexible circuit card 12. Reference electrode 14 is formed of a silver wire jacketed sectionally with PEEK. On an end, advantageously its sensor element end, the silver wire is connected, for example, by means of a soldered connection, conductively with an additional conductive trace of the flexible circuit card, which likewise is connected with the sensor circuit 13. On its other end, the silver wire has an AgCl coating and extends in an inner electrolyte 15 contained in the sensor body 4. In the present example, the inner electrolyte 15 is an aqueous, 3 molar, KCl solution. The inner electrolyte can also be a gel electrolyte, which can be composed of a solution of a polymer with embedded KCl. Via a macroporous diaphragm 16, for example, of ceramic, arranged in the housing wall of the sensor body 4, the inner electrolyte 15 is in electrolytic contact with a medium surrounding the front end region of the sensor 1, so that charge transport can occur between the inner electrolyte 15 and the surrounding medium.

Housing 3 is cast in its front end region, for instance, up to the height of the bulwark 11, with a potting compound, for example, an epoxide resin, so that especially the sensor element end of the reference electrode 14 connected with the flexible circuit card as well as its joint with the conductive trace serving as potential sensing lead are both isolated from the inner electrolyte 15.

Circuit card 12 serves consequently for connecting both the sensor element 2 as well as also the reference electrode 14 with the sensor circuit. In such case, such as initially indicated, the conventional dividing of the housing in two into an inner space, in which the connection wires of the sensor element extend, and an additional space containing the inner electrolyte is not used, which means, on the one hand, that the manufacturing of the sensor 1 is simplified and, on the other hand, that more space is available internally in the sensor.

In the front end potted region of the housing 3, preferably as near as possible to the sensor element 2, there is supplementally arranged on the flexible circuit card 12 a temperature sensor 22, which is connected with an additional conductive trace of the flexible circuit card 12. This additional conductive trace is, same as the potential sensing conductive trace of the reference electrode 14 and the conductive traces connected with the sensor element 2, connected with the sensor circuit 13, which registers and processes the signals provided by the temperature sensor 22.

Arranged in the tubular section of the sensor body 4 forming the sensor shaft is a seal 17, which divides the sensor housing into a first chamber 18 and a second chamber 19. The first chamber 18 is located in the sensor body 4 and contains the reference electrolyte 15. The second chamber 19 is formed by the rear end section of the sensor body 4 and the electronics housing part 5 plugged thereon. Arranged in this second chamber 19 is the sensor circuit 13. Seal 17 is formed in the example shown here by two adjoining, elastic sealing elements 23, 24, which fill the cross section of the sensor shaft and bear against its inner wall, so that the circuit card 12 led between the sealing elements 23, 24 from the first into the second chamber is clamped between two adjoining sealing surfaces of the sealing elements 23, 24. In this way, the second chamber 19 containing the sensor circuit 13 remains tightly sealed relative to the first, electrolyte filled chamber 18, so that no inner electrolyte 15 can penetrate into the second chamber 19.

Figure 3:
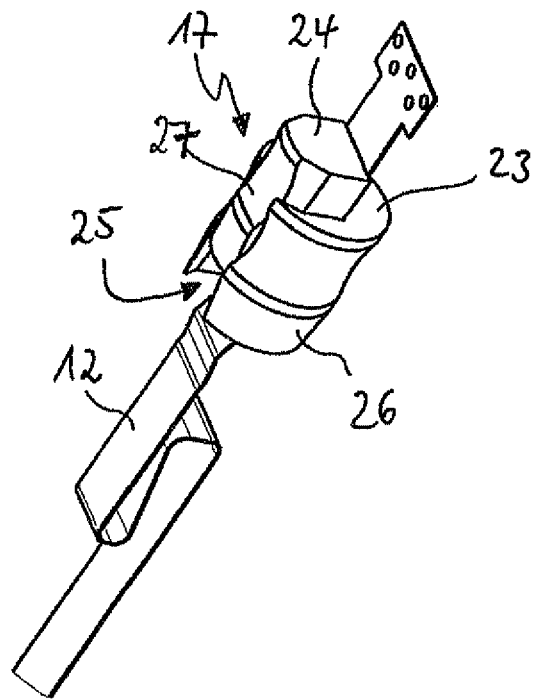
FIG. 3 is a detail view of a flexible circuit card contained in the sensor illustrated in FIG. 1, with a sealing arrangement in a first position.
Figure 4:
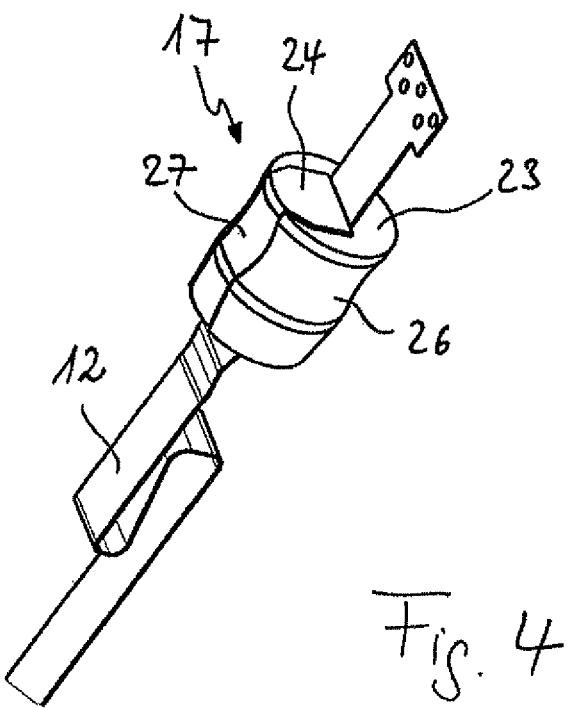
FIG. 4 is a detail view of the circuit card illustrated in FIG. 3, with the sealing arrangement in a second position.

Seal 17 is presented in detail in FIGS. 3 and 4. The sealing elements 23, 24 can, in the example shown here, be joined to form a rotationally symmetric, plug-like seal 17. A first sealing element 23 has, extending axially relative to the rotational symmetry axis of the seal 17, a groove 25, into which the second sealing element 24, such as can be seen in FIG. 3, is insertable. The flexible circuit card 12 can be placed against an area of the first sealing element 23 within the groove 25 and is clamped in the case of assembled seal 17 between this area and a thereto abutting area of the second sealing element 24. The sealing elements 23, 24 bear with their side surfaces 26, 27 against the inner wall of the tubular sensor shaft, and so seal the first chamber 18 liquid tightly relative to the second chamber 19.

Additionally, the region between the seal 17 and the end of the sensor body 3 open toward the sensor rear can be filled with a potting compound.

The flexible circuit card has within the first chamber 18 an "S" fold, so that the length of the flexible circuit card between the sensor element 2 and the seal 17 is greater than the separation between the seal 17 and the sensor element 2. This serves, on the one hand, for strain relief of the flexible circuit card 12. On the other hand, it becomes possible, due to the space saving within the sensor body 4 as a result of the omission of a supplemental, internal tube, to manufacture different sensor types of different lengths by applying flexible circuit cards of one and the same length, wherein the circuit card 12 can be folded one or more times, when the sensor body 4 is markedly shorter than the circuit card 12.

In the example shown here, sensor circuit 13 is arranged on a rigid circuit card 20. The conductive traces of the flexible circuit card 12 connected with the contact elements of the sensor element 2 and the reference electrode 14 are connected with associated connections of the sensor circuit 13. For additionally simplifying the manufacturing of the sensor 1, the connectors of the flexible circuit card 12 and the rigid circuit card 20 are matched to one another.

The second chamber 19 can be filled e.g. with an epoxide resin. Especially, the potting compound can be cast onto the sensor circuit 13.

Sensor circuit 13 includes, besides means for additional processing of the measuring signals, especially their amplification and digitizing, a memory for storing sensor data and/or measured values. Along with that, the circuit in the example shown here includes an inductive interface 21 integrated into a mechanical, sensor plug head. This interface 21 can be connected with a complementary socket (not shown), in order to connect the sensor 1 with a superordinated unit, for example, a measurement transmitter, a conventional computer or a bus coupler. Data, especially measured values, and energy can be transmitted over the inductive interface.

The invention claimed is:

1. A sensor for registering an analyte concentration, comprising:
a housing;
a sensor element arranged within said housing, said sensor element has a front surface pressed toward a housing wall of said housing, wherein said housing wall has an opening exposing an analyte sensitive region of said front surface;
at least one contact element for electrical contacting said sensor element;
an inner electrolyte which is in contact with a medium surrounding said housing via an electrochemical, liquid junction arranged in a housing wall; and
a reference electrode extending into said inner electrolyte, wherein:
there is arranged within said housing a flexible circuit card, which includes at least a first conductive trace, which is connected with said at least one contact element of said sensor element, and at least a second conductive trace, which serves as a potential sensing element of said reference electrode.

2. The sensor as claimed in claim 1, wherein:
said inner electrolyte is contained in a first chamber formed within said housing;
said housing has, sealed from said first chamber, a second chamber, in which a sensor circuit, is accommodated; and
said first chamber is sealed from said second chamber, by means of at least one seal, through which said flexible circuit card is led.

3. The sensor as claimed in claim 2, wherein:
said first and said second conductive traces are connected electrically conductively with said sensor circuit.

4. The sensor as claimed in claim 2, wherein:
said sensor circuit is arranged within said second chamber on a circuit card, which is coupled with said flexible circuit card in such a manner that said first and said second conductive traces are connected electrically conductively with said sensor circuit.

5. The sensor as claimed in claim 2, wherein:
said housing comprises a sensor body and an electronics housing part fixedly connected with said sensor body;
said sensor body has an at least sectionally tubular, sensor shaft and, adjoining said sensor shaft frontally, an end section, which includes the housing wall, toward which the front surface of said sensor element is pressed; and
a rear end of said sensor shaft is closed by said electronics housing part.

6. The sensor as claimed in claim 5, wherein:
there is arranged in a rear end region of said sensor shaft for sealing said first chamber relative to said second chamber a seal, which comprises, biased toward one another, at least two sealing elements of synthetic material, between which said flexible circuit card is clamped.

7. The sensor as claimed in claim 5, wherein:
said electronics housing part includes an interface for connecting to a superordinated unit.

8. The sensor as claimed in claim 1, wherein:
said reference electrode comprises an at least sectionally chlorided silver wire connected with said second conductive trace.

9. The sensor as claimed in claim 1, wherein:
said reference electrode comprises a silver layer arranged on said flexible circuit card and in electrical contact with said second conductive trace.

10. The sensor as claimed in claim 1, wherein:
the electrically conductive connection, between said reference electrode and said flexible circuit card is arranged in a frontal region of said flexible circuit card.

11. The sensor as claimed in claim 1, wherein:
said flexible circuit card includes an additional, shielding ply.

12. The sensor as claimed in claim 1, wherein:
said flexible circuit card is equipped in the region of said sensor element with a temperature sensor, which is connected with a third conductive trace of said flexible circuit card.

13. The sensor as claimed in claim 12, wherein:
said third conductive trace is connected with said sensor circuit.

14. The sensor as claimed in claim 1, wherein:
said sensor element comprises an EIS structure.

15. The sensor as claimed in claim 1, wherein:
said sensor element comprises an ion sensitive field effect transistor (ISFET), which comprises, besides the analyte sensitive region serving as gate on the front surface, a source connection arranged on the front surface of said sensor element and serving as contact element and a drain connection arranged on the front surface of said sensor element and serving as a further contact element.

16. The sensor as claimed in claim 1, wherein:
said sensor element comprises' an ion sensitive field effect transistor (ISFET), which comprises, besides the analyte sensitive region serving as gate on the front surface, a source connection arranged on a rear surface of said sensor element and serving as contact element and a drain connection arranged on the rear surface of said sensor element and serving as a further contact element.

17. The sensor as claimed in claim 1, wherein:
the flexible circuit card comprises an electrically insulating base material; and
the first and second conductive traces extend within the base material or are covered by an additional coating of a plastic material.

18. The sensor as claimed in claim 17, wherein:
the flexible circuit card is located directly in the inner electrolyte.

19. A sensor for registering an analyte concentration, comprising:
- a housing;
- a sensor element arranged within said housing, said sensor element has a front surface pressed toward a housing wall of said housing,
- wherein said housing wall has an opening exposing an analyte sensitive region of said front surface;
- at least one contact element for electrical contacting said sensor element; an inner electrolyte which is in contact with a medium surrounding said housing via an electrochemical, liquid junction arranged in a housing wall; and
- a reference electrode extending into said inner electrolyte, wherein:
- there is arranged within said housing a flexible circuit card, which includes at least a first conductive trace, which is connected with said at least one contact element of said sensor element, and at least a second conductive trace, which serves as a potential sensing element of said reference electrode; and
- the electrically conductive connection between said reference electrode and said flexible circuit card is arranged in a frontal region of said flexible circuit card.

20. The sensor as claimed in claim 19, wherein:
- the electrically conductive connection between said reference electrode and said flexible circuit card is arranged in the frontal region of said flexible circuit card in the vicinity of said sensor element.

21. The sensor as claimed in claim 20, wherein:
- a frontal end region of said housing, in which the sensor element and the electrically conductive connection between said reference electrode and said flexible circuit card is arranged, is filled with a potting compound.

* * * * *